United States Patent
Tainaka

(10) Patent No.: US 10,473,634 B2
(45) Date of Patent: Nov. 12, 2019

(54) DATA PROCESSING DEVICE FOR MASS SPECTROMETRY AND PROGRAM FOR SAID DEVICE

(71) Applicant: SHIMADZU CORPORATION, Kyoto-shi, Kyoto (JP)

(72) Inventor: Yoshiki Tainaka, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 408 days.

(21) Appl. No.: 15/317,738

(22) PCT Filed: Jun. 12, 2014

(86) PCT No.: PCT/JP2014/065580
§ 371 (c)(1),
(2) Date: Dec. 9, 2016

(87) PCT Pub. No.: WO2015/189949
PCT Pub. Date: Dec. 17, 2015

(65) Prior Publication Data
US 2017/0108478 A1    Apr. 20, 2017

(51) Int. Cl.
*G01N 30/72*    (2006.01)
*H01J 49/26*    (2006.01)
(Continued)

(52) U.S. Cl.
CPC ..... *G01N 30/8658* (2013.01); *G01N 30/7233* (2013.01); *H01J 49/0036* (2013.01)

(58) Field of Classification Search
CPC .. H01J 49/0036; H01J 49/0031; H01J 49/063; H01J 49/26; H01J 49/426;
(Continued)

(56) References Cited

U.S. PATENT DOCUMENTS 5,986,259 A * 11/1999 Hirabayashi ......... H01J 49/044
250/281
10,198,630 B2 * 2/2019 Noda ................. G01N 30/8634
(Continued)

FOREIGN PATENT DOCUMENTS

| JP | 2007-046966 A | 2/2007 |
| JP | 2011-242255 A | 12/2011 |
| JP | 2013-195099 A | 9/2013 |

OTHER PUBLICATIONS

Written Opinion for PCT/JP2014/065580 dated Jul. 15, 2014. [PCT/ISA/237].
(Continued)

*Primary Examiner* — David A Vanore
(74) *Attorney, Agent, or Firm* — Sughrue Mion, PLLC

(57) ABSTRACT

A check condition setting screen, for confirming, whether a target ion originates from a target compound, is provided with qualifier ion mode choices: "ABSOLUTE TOLERATION," "RELATIVE TOLERATION", and "ABSOLUTE TOLERATION OR RELATIVE TOLERATION". When the "ABSOLUTE TOLERATION OR RELATIVE TOLERATION" mode is set, an identification range Pa is calculated from a qualifier ion ratio reference value and an absolute tolerance, and an identification range Pr is calculated from the qualifier ion ratio reference value and a relative tolerance, for each qualifier ion for one target ion, and whichever of the two identification ranges is the greater is selected. In addition, when a setting to limit the upper limit value of an identification range to 100% is enabled, the upper limit value of the identification range is limited to 100%, and when the lower limit value of the identification range exceeds 100%, a warning display indicating above upper limit is performed.

17 Claims, 3 Drawing Sheets

(51) Int. Cl.
*G01N 30/86* (2006.01)
*H01J 49/00* (2006.01)

(58) Field of Classification Search
CPC .... G01N 30/72; G01N 27/62; G01N 30/8631; G01N 30/86; G01N 30/8644; G01N 30/8658; G01N 30/8634; G01N 30/8637; G01N 30/8651; G01N 30/8696
USPC .................. 250/281, 282, 288; 702/189, 23
See application file for complete search history.

(56) References Cited

U.S. PATENT DOCUMENTS

| | | | | |
|---|---|---|---|---|
| 10,229,822 | B2* | 3/2019 | Mizutani | H02M 7/10 |
| 10,236,167 | B1* | 3/2019 | Noda | H01J 49/40 |
| 2004/0181351 | A1* | 9/2004 | Thompson | G01N 30/72 |
| | | | | 702/76 |
| 2010/0213368 | A1* | 8/2010 | Wang | H01J 49/0036 |
| | | | | 250/282 |
| 2016/0025691 | A1* | 1/2016 | Taneda | G01N 30/8637 |
| | | | | 702/23 |
| 2016/0033458 | A1* | 2/2016 | Maeda | G01N 30/86 |
| | | | | 702/189 |
| 2016/0209378 | A1* | 7/2016 | Kobayashi | G01N 30/72 |
| 2016/0329203 | A1* | 11/2016 | Fujita | H01J 49/107 |
| 2017/0067864 | A1* | 3/2017 | Kudo | H01J 49/0036 |
| 2017/0108478 | A1* | 4/2017 | Tainaka | G01N 30/7233 |
| 2017/0138916 | A1* | 5/2017 | Sumiyoshi | G01N 30/7233 |
| 2017/0287691 | A1* | 10/2017 | Asano | H01J 49/0031 |
| 2017/0328874 | A1* | 11/2017 | Yamamoto | G01N 30/8644 |
| 2018/0284065 | A1* | 10/2018 | Yamamoto | G01N 27/62 |
| 2018/0337028 | A1* | 11/2018 | Nakaya | G01N 27/62 |
| 2019/0079051 | A1* | 3/2019 | Satake | G01N 27/622 |
| 2019/0087158 | A1* | 3/2019 | Yamamoto | G06F 7/523 |

OTHER PUBLICATIONS

Shigemi Kai, et al., "Analysis 5 of deoxynivelenol in grain using liquid chromatography / tandem mass spectrometry", Bulletin of Kanagawa Prefectural Institute of Public Health (Bull. Kanagawa Ins. of P.H.), No. 37 (2007), searched on May 13, 2014, <URL: http://www.eiken.pref.kanagawa.jp/004_chousa/04_research/files/37_PDF/37-8.pdf>.

"AORC Guidelines for the Minimum Criteria for Identification by Chromatography and Mass Spectrometry", Association of Official Racing Chemists (AORC), Searched on May 16, 2014 <URL: http://www.aorconline.org/documents/aorc-ms-criteria-may-2011/aorc-ms-criteria-may-2011.pdf>.

"Identification criteria for residues determined by LC-MS/MS: are they fit-for-purpose?", EURL-FV, Searched on May 16, 2014, <http://www.eurl-pesticides.eu/userfiles/file//13-Hans_Mol.pdf>.

Nicolaas (Klaas) M. Faber, "Regulations in the field of residue and doping analysis should ensure the risk of the false positive declaration is well-defined", Accreditation and Quality Assurance, Nov. 11, 2008, pp. 111-115, vol. 14, No. 2.

International Search Report for PCT/JP2014/065580 dated Jul. 15, 2014.

Communication dated Aug. 28, 2018 from the State Intellectual Property Office of People's Republic of China in counterpart Chinese Patent Application No. 201480079798.1.

* cited by examiner

Fig. 6

| # | m/z | ION RATIO | TOLERANCE | IDENTIFICATION RANGE (%) |
|---|---|---|---|---|
| 1 | 147.00>74.00 | 10.00 | DEFAULT | 0.00-100.00 |
| 2 | 130.00>41.00 | 60.00 | DEFAULT | 0.00-100.00 |
| 3 | 251.00>59.00 | 150.00 | DEFAULT | 90.00-100.00 |
| 4 | 130.00>29.00 | 200.00 | 60 | ABOVE UPPER LIMIT |
| 5 | 130.00>27.00 | 300.00 | DEFAULT | ABOVE UPPER LIMIT |

QUALIFIER ION RATIO   ID# 7 -Target m/z: 147.00>46.00

Fig. 7

| # | ION RATIO (%) | IDENTIFICATION RANGE (%) |
|---|---|---|
| 1 | 0 - 10 | 5 - 15 |
| 2 | 10 - 50 | 5 - 60 |
| 3 | 50 - 80 | 30 - 95 |

Fig. 8

CONFIRMATION ON SPECTRUM

☑ USE QUALIFIER ION
QUALIFIER ION MODE:  ABSOLUTE TOLERATION ▼
  ABSOLUTE TOLERATION
  RELATIVE TOLERATION
  CALCULATION ONLY
ION RATIO TOLERANCE:
QUALIFIER ION BASE:
  ⦿ SPECTRUM   ○ WAVEFORM PROCESSING RESULT
QUALIFIER ION RATIO CORRECTION:
  ⦿ UNCHANGE   ○ REPLACEMENT   ○ AVERAGE

Fig. 9

QUALIFIER ION RATIO   ID# 18 -Target m/z: 147.00>46.00

| # | m/z | ION RATIO | TOLERANCE | IDENTIFICATION RANGE (%) |
|---|---|---|---|---|
| 1 | 147.00>74.00 | 50.00 | DEFAULT | 20.00-80.00 |
| 2 | 130.00>41.00 | 60.00 | DEFAULT | 30.00-90.00 |
| 3 | 130.00>29.00 | 70.00 | DEFAULT | 40.00-100.00 |
| 4 | 130.00>27.00 | 80.00 | DEFAULT | 50.00-110.00 |
| 5 | 251.00>59.00 | 90.00 | DEFAULT | 60.00-120.00 |

DATA PROCESSING DEVICE FOR MASS SPECTROMETRY AND PROGRAM FOR SAID DEVICE

CROSS REFERENCE TO RELATED APPLICATIONS

This application is a National Stage of International Application No. PCT/JP2014/065580 filed Jun. 12, 2014, the contents of all of which are incorporated herein by reference in their entirety.

TECHNICAL FIELD

The present invention relates to a data-processing system for processing data collected using a mass spectrometer and a computer program for the system, more in detail to a data-processing system for making a quantitative determination on a compound in a sample by means of mass spectrometry and a program for the system.

BACKGROUND ART

In a chromatographic mass spectrometer, a combination of a gas chromatograph (GC) or a liquid chromatograph (LC), and a mass spectrometer, various components contained in a sample to be tested are temporally separated through a column, and ions generated from the separated components are separated according to their mass-to-charge ratios m/z through a quadrupole mass filter or the like to be detected by a detector.

To make a quantitative determination on a known compound contained in a sample using such a chromatographic mass spectrometer, in general, an ion characterizing the compound is determined to be a target ion, and the target ion is subjected to selected ion monitoring (SIM) measurement or multiple reaction monitoring (MRM) measurement by the mass spectrometer. Then, based on data obtained from the measurement, an extracted-ion chromatogram (mass chromatogram) for the target ion is created, and the concentration of the target compound is calculated from the area, the height or the like of a chromatogram peak appearing at around the retention time of the target compound on the chromatogram. The target ion may also be referred to as a quantitative ion, and as such, an ion corresponding to a peak of a maximum signal intensity on a typical mass spectrum of the compound is normally selected.

Although a target ion is an ion characterizing a compound, various impurities may be included in an actual sample, or inappropriate separation conditions in a previous-stage chromatograph may result in insufficient component separation, making a plurality of compounds overlap one another. In such cases, only checking a chromatogram peak of a target ion having a specified mass-to-charge ratio $M_T$ makes it difficult to clearly determine whether or not the peak originates from a target compound. Therefore, in quantitative analysis using a chromatographic mass spectrometry, in general, an ion that characterizes the compound but has another mass-to-charge ratio $M_C$ is selected as a qualifier ion in addition to a target ion, and using intensity ratio between the signal intensity of the peak of the qualifier ion and the signal intensity of the peak of the target ion on a mass spectrum in actual measurement (hereafter, referred to as "qualifier ion ratio"), the confirmation of the target ion truly originating from a target compound, that is, the identification of the target ion is performed (see Patent Literature 1 and Non Patent Literature 1). In addition, for example, in the case where a plurality of compounds similar in structure are possibly contained in a sample, only one kind of qualifier ion may be insufficient to correctly identify a target ion of a certain compound, and thus a plurality of qualifier ions are often used for one compound.

In the case of simultaneous multiple-component analysis, quantitative determination may be performed on a large number of compounds as many as several tens, or several hundreds in some cases, at one time of chromatographic mass spectrometry. However, it is difficult for an operator to visually determine whether or not qualifier ion ratios are appropriate for such a large number of compounds. Thus, a conventional chromatographic mass spectrometer includes a determined identification range having a tolerance preset for each qualifier ion ratio and is configured to automatically execute a process in which a target ion is identified as an ion originating from a target compound when qualifier ion ratios in actual measurement fall within respective identification ranges (see Patent Literature 2, etc.).

FIG. 8 is a diagram illustrating a parameter setting screen for qualifier ions used to execute such an automated process in the conventional chromatographic mass spectrometer, and FIG. 9 is a diagram illustrating an advanced setting screen for qualifier ions for each target ion.

A method for identifying a target ion using qualifier ions includes two modes: "ABSOLUTE TOLERATION" and "RELATIVE TOLERATION". The absolute toleration is a mode in which an identification range used to identify a target ion as one originating from a target compound is specified literally in the form of the absolute value of a qualifier ion ratio, and assuming that the qualifier ion ratio is denoted by Ri[%], and the tolerance is denoted by Rw[%], an identification range Pa is defined as follows.

$$Pa = Ri \pm Rw[\%] \quad (1)$$

Meanwhile, the relative toleration is a mode in which an identification range is specified in the form of the relative ratio of a qualifier ion ratio, and assuming that the qualifier ion ratio is denoted by Ri[%], and the tolerance is denoted by Rw[%], an identification range Pr is defined as follows.

$$Pr = Ri \pm (Ri \times Rw)/100[\%] \quad (2)$$

In the qualifier ion parameter setting screen illustrated in FIG. 8, one of "ABSOLUTE TOLERATION" and "RELATIVE TOLERATION" is selectable as a qualifier ion mode by means of a drop-down menu, and when a qualifier ion ratio and a tolerance for a certain qualifier ion are given, an identification range is set according to the previously described Equation (1) or (2). Specifically, FIG. 9 is an advanced setting screen for qualifier ions illustrating the identification ranges of five qualifier ions for a target ion having a precursor ion m/z: 147.00, and a product ion m/z: 46.0 (m/z: 147.00>46.0) in MRM measurement. In this example, the qualifier ion mode is the absolute toleration, a default tolerance is ±30[%], and for example, for a qualifier ion having a qualifier ion ratio of 60.00, a precursor ion m/z: 130.00, and a product ion m/z: 41.0, an identification range from a lower limit of 60−30=30 to an upper limit of 60+30=90 is set. With this setting, for this qualifier ion, when a qualifier ion ratio based on an actually measured result falls within this identification range, a target ion of m/z: 147.00>46.0 is identified to originate from the target compound.

However, the conventional chromatographic mass spectrometer described previously involves the following problems. That is, while an operator can select either one of the absolute toleration and the relative toleration as the qualifier ion mode, the absolute toleration and the relative toleration may need to be combined for some purpose or application of measurement.

For example, the guidelines on drug test by Association of Official Racing Chemists (AORC), disclosed in Non Patent Literature 2, specify that a qualifier ion ratio in the absolute toleration and a qualifier ion ratio in the relative toleration are separately set, identification ranges in both modes are calculated using the separately set qualifier ion ratios, and whichever of an absolute tolerance and a relative tolerance is greater is employed as an identification range for the target ion identification. In addition, the previously described AORC guidelines specify that the upper limit of an identification range is 100% (i.e., specify that identification is disabled when the signal intensity of a qualifier ion exceeds the signal intensity of a target ion).

Meanwhile, with the conventional chromatographic mass spectrometer described previously, target ion identification consistent with such guidelines cannot be automatically performed, and thus the operator has to confirm whether or not a qualifier ion ratio is within an identification range, which requires very cumbersome operations. In addition, a qualifier ion ratio cannot be separately set for the absolute toleration and the relative toleration, and thus the operator has to set an identification range for the absolute toleration and an identification range for the relative toleration one by one. In addition, the operator has to modify identification ranges exceeding 100% one by one, which is very troublesome.

In addition, according to the identification criteria for pesticide residues in EU disclosed in Non Patent Literature 3, a recommended tolerance differs by qualifier ion. To set such a recommended tolerance in the conventional chromatographic mass spectrometer described previously, the operator has to confirm a qualifier ion ratio set for each qualifier ion and set a tolerance corresponding to the qualifier ion ratio, which is very troublesome.

CITATION LIST

Patent Literature

[Patent Literature 1] JP 2011-242255 A
[Patent Literature 2] JP 2013-195099A

Non Patent Literature

[Non Patent Literature 1] Shigemi KAI, et al., "Analysis of deoxynivelenol in grain using liquid chromatography/tandem mass spectrometry", Bulletin of Kanagawa Prefectural Institute of Public Health (Bull. Kanagawa Ins. of P.H.), No. 37 (2007), searched on May 13, 2014 on the Internet
[Non Patent Literature 2] "AORC Guidelines for the Minimum Criteria for Identification by Chromatography and Mass Spectrometry", Association of Official Racing Chemists (AORC), Searched on May 16, 2014 on the Internet
[Non Patent Literature 3] "Identification criteria for residues determined by LC-MS/MS: are they fit-for-purpose?", EURL-FV, Searched on May 16, 2014 on the Internet

SUMMARY OF INVENTION

Technical Problem

The present invention has been developed in light of the previously described problem. Its objective is to provide a data-processing system for mass-spectrometry that allows appropriate determination according to various guidelines to be conducted while reducing the workload on the operator in operation, for the confirmation of, using a qualifier ion ratio, whether or not a target ion is an appropriate ion originating from a target compound, even in the case where the number of target compounds is large, or the number of qualifier ions for one target ion is large, and to provide a program for the system.

Solution to Problem

A data-processing system for mass-spectrometry according to the present invention, which has been made to solve the previously described problem, is a data-processing system for mass-spectrometry that, with a predetermined qualifier ion for confirming a target compound having a different mass-to-charge ratio from that of a target ion characterizing the target compound and having a specified mass-to-charge ratio, calculates signal intensities of the target ion and the qualifier ion calculated through measurement on a target sample, and confirms an appropriateness of the target ion using a result of the calculation for identification or quantitative determination of the target compound, and the data-processing system includes:

a) a mode selection section for allowing a user to select one of a first mode, a second mode, and a third mode in order to determine an identification range of a qualifier ion ratio, the qualifier ion ratio being an intensity ratio between a signal intensity of the target ion and a signal intensity of the qualifier ion, the identification range being used to determine whether or not a peak on a mass spectrum supposed to be a peak of a target ion originating from target compound truly originates from the target compound, the first mode being a mode in which a tolerance of a qualifier ion ratio is determined in a form of an absolute value of the ratio, the second mode being a mode in which a tolerance of a qualifier ion ratio is determined in a form of a relative value of the ratio, and the third mode being a mode in which a tolerance of a qualifier ion ratio is selected from one of an identification range of a qualifier ion ratio determined in the form of an absolute value of the ratio and an identification range of a qualifier ion ratio determined in the form of a relative value of the ratio according to comparison between the identification ranges; and b) an identification range determination section configured to, when the third mode is selected, calculate a first identification range based on an absolute tolerance given as an absolute value of the ratio and a second identification range based on a relative tolerance given as a relative value of the ratio with respect to a standard qualifier ion ratio for a qualifier ion of interest, select one of the two identification ranges, the first and second identification ranges, according to comparison between the first and second identification ranges, and determine the selected identification range to be an identification range used to determine an actually measured qualifier ion ratio.

In addition, a program for data processing according to the present invention, which has been made to solve the previously described problem, is a program, running on a computer, for a data-processing system that, with a predetermined qualifier ion for confirming a target compound having a different mass-to-charge ratio from that of a target ion characterizing the target compound and having a specified mass-to-charge ratio, calculates signal intensities of the target ion and the qualifier ion calculated through measurement on a target sample, and confirms an appropriateness of the target ion using a result of the calculation for identification or quantitative determination of the target compound, the program causing the computer to operate as:

a) a mode selection section for allowing a user to select one of a first mode, a second mode, and a third mode in order to determine an identification range of a qualifier ion ratio, the qualifier ion ratio being an intensity ratio between a signal intensity of the target ion and a signal intensity of the qualifier ion, the identification range being used to determine whether or not a peak on a mass spectrum supposed to be a peak of a target ion originating from target compound truly originates from the target compound, the first mode being a mode in which a tolerance of a qualifier ion ratio is determined in a form of an absolute value of the ratio, the second mode being a mode in which a tolerance of a qualifier ion ratio is determined in a form of a relative value of the ratio, and the third mode being a mode in which a tolerance of a qualifier ion ratio is selected from one of an identification range of a qualifier ion ratio determined in the form of an absolute value of the ratio and an identification range of a qualifier ion ratio determined in the form of a relative value of the ratio according to comparison between the identification ranges; and b) an identification range determination section configured to, when the third mode is selected, calculates a first identification range based on an absolute tolerance given as an absolute value of the ratio and a second identification range based on a relative tolerance given as a relative value of the ratio with respect to a standard qualifier ion ratio for a qualifier ion of interest, select one of the two identification ranges, the first and second identification ranges, according to comparison between the first and second identification ranges, and determine the selected identification range to be an identification range used to determine an actually measured qualifier ion ratio.

The data-processing system for mass-spectrometry according to the present invention can be embodied typically by a computer with the program for data processing according to the present invention running on it.

In the data-processing system for mass-spectrometry according to the present invention, in the mode selection section, a user (operator) can select the first mode (an absolute toleration mode) and the second mode (a relative toleration mode) provided in conventional systems, as well as a third mode. This mode selection section may be configured to specify one of the three modes by means of a pull-down menu, a radio button, or the like displayed on a screen of a display unit. When the user selects the third mode on the mode selection section, the identification range determination section calculates a first identification range based on an absolute tolerance and a second identification range based on a relative tolerance for each of standard qualifier ion ratios for qualifier ions of interest. For the absolute toleration and the relative toleration, respective default values are determined, and these default values may be applied to all qualifier ions in common unless the user changes the settings.

Meanwhile, even in the case where a plurality of qualifier ions are determined for one target ion, changing an absolute tolerance or a relative tolerance for qualifier ion may be intended in such a case such as conducting measurement consistent with the criteria disclosed in Non Patent Literature 3. Thus, the data-processing system for mass-spectrometry according to the present invention preferably further includes a tolerance setting section that allows a user to input an absolute tolerance and a relative tolerance for each qualifier ion.

The tolerance setting section described previously may be configured to display, for example, a table in a screen identical to or separated from the display screen for selection in the mode selection section, the table indicating an absolute tolerance and a relative tolerance for each qualifier ion and to receive input of a tolerance in the form of a numerical value in the table as necessary. When the first or the second modes is selected in the mode selection section, only one of the absolute tolerance and the relative tolerance is used. Therefore, in this case, the table may include only a column of absolute tolerance or relative tolerance. This configuration prevents displaying parameters that need not be input or confirmed in the case of using one of the first and the second modes provided in conventional systems, which assures similar operability as with conventional systems.

In any case, when the first and the second identification ranges are calculated based on predetermined absolute tolerance and relative tolerance, the identification range determination section, for example, compares both identification ranges and selects whichever is the greater, and determines the greater as an identification range. After the determination of the identification range in such a manner, for example, whether or not a qualifier ion ratio based on an actually measured result is within this identification range is automatically determined, and when the qualifier ion ratio falls within the identification range, it is estimated that a target ion is likely to be an ion originating from a target compound.

The data-processing system for mass-spectrometry according to the present invention may further include a range limit setting section that allows a user to specify an upper limit and/or a lower limit of an identification range to determine an actually measured qualifier ion ratio.

Typically, the upper limit of an identification range may be allowed to be set at 100% so that the identification of a target ion is determined to be disabled when a qualifier ion ratio exceeds 100%.

In such a configuration, the identification range determination section may be further configured to narrow the identification range in accordance with a predetermined upper limit value or lower limit value when the upper limit and/or the lower limit is specified in the range limit setting section.

With this configuration, when the upper limit value of the identification range selected by the identification range determination section through the comparison between the first and the second identification ranges exceeds 100%, for example, the upper limit of the identification range will be limited to 100%. This allows the upper limit of an identification range used for the determination of an actually measured qualifier ion ratio to be set at any value, for example, 100%, irrespective of an identification range calculated from a reference value of a qualifier ion ratio, and an absolute tolerance or a relative tolerance.

When part of a calculated identification range falls within a range constrained by an upper limit and/or a lower limit specified by the range limit setting section, identification using a qualifier ion ratio can be performed. However, when the entire calculated identification range falls out of the range constrained by the upper limit and/or the lower limit specified by the range limit setting section, identification using the qualifier ion ratio is disabled in the first place. Thus, the data-processing system for mass-spectrometry according to the present invention may include a notification section that allows a user to be notified of the fact that an upper limit and/or a lower limit is specified by the range limit setting section, and the calculated entire identification range falls out of a range constrained by a predetermined upper limit value or lower limit value.

For example, the notification section may be configured to display that identification is disabled, in place of the displaying indicating an identification range. This configuration allows a user to immediately recognize that a specified qualifier ion, or a reference value, a tolerance, or the like of a qualifier ion ratio for determining an identification range is inappropriate.

Some mass spectrometers or chromatographic mass spectrometers have a function of automatically creating and displaying or printing a report in a predetermined format to which analyzing results, analysis conditions, data analysis conditions, and the like are attached. Thus, the data-processing system for mass-spectrometry according to the present invention may further include an output unit configured to output an identification range determined by the identification range determination section in the form of a report. This configuration allows an identification range used for the identification of a target ion to be put in the report as one of the data analysis conditions.

Advantageous Effects of Invention

With the mass spectrometry data-processing system and the program for data processing according to the present invention, even in the case where a target ion needs to be confirmed consistent with the guidelines disclosed in Non Patent Literature 2 or the like, it is possible to determine an appropriate identification range and determine whether or not a qualifier ion ratio is suitable while the operator need not perform cumbersome and laborious operations of calculation and comparison. Therefore, even in the case where the number of target compounds or the number of qualifier ions for one target ion is large, it is possible to proceed with substance identification operation or quantitative operation by determining whether or not a target ion is appropriate, in a short time, efficiently, and preventing the occurrence of an operation error.

BRIEF DESCRIPTION OF DRAWINGS

FIG. 6 is a diagram illustrating still another example of a qualifier ion advanced setting screen for each target ion in the LC-MS/MS system in the present embodiment.

FIG. 7 is a diagram for illustrating a modification of the data-processing system according to the present invention.

FIG. 8 is a diagram illustrating an example of a spectrum check condition setting screen in a conventional chromatographic mass spectrometer.

FIG. 9 is a diagram illustrating an example of a qualifier ion advanced setting screen for each target ion in a conventional chromatographic mass spectrometer.

DESCRIPTION OF EMBODIMENTS

Figure 1:
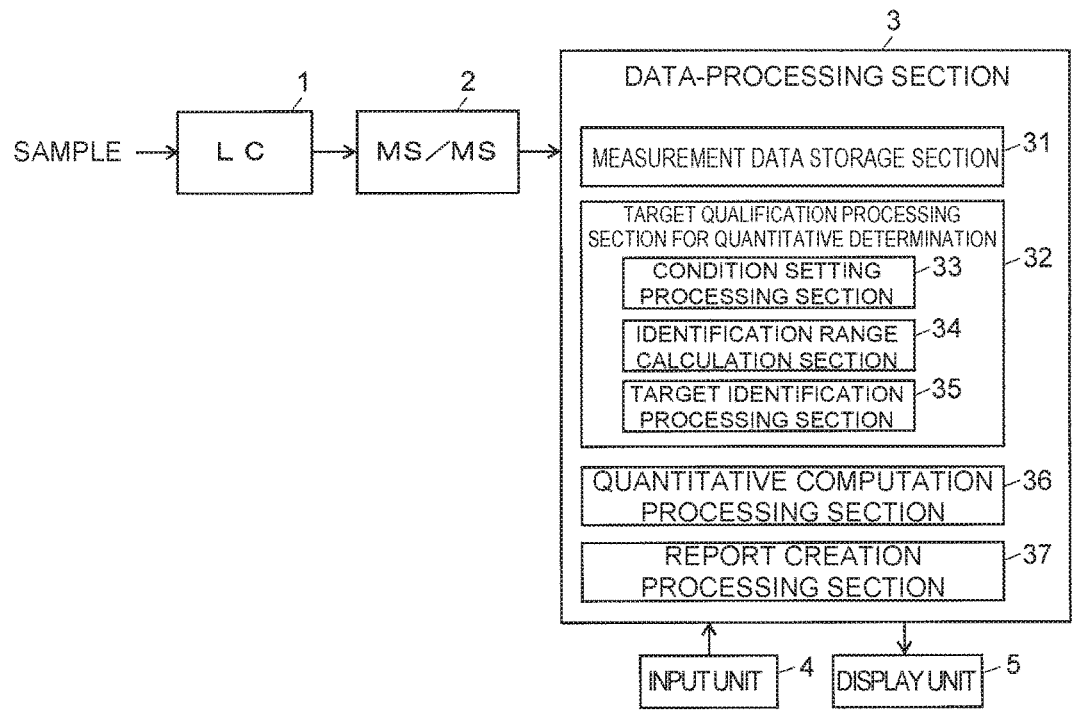
FIG. 1 is a schematic configuration diagram in an embodiment of an LC-MS/MS system including a data-processing system according to the present invention.

An LC-MS/MS system including a data-processing system for mass-spectrometry according to the present invention is hereinafter described with reference to the attached drawings. FIG. 1 is a schematic configuration diagram of the LC-MS/MS system according to the present embodiment.

The system includes a liquid chromatograph (LC) 1 that temporally separates components in a sample, a mass spectrograph (MS/MS) 2 such as a tandem quadrupole mass spectrograph that performs MS/MS measurement on ions generated by ionizing the components separated by the liquid chromatograph 1, using an atmospheric pressure ion source by electrospray ionization (ESI), a data-processing section 3 that processes data acquired by the mass spectrograph 2, an input unit 4 including a keyboard and a pointing device such as a mouse operated by an operator, and a display unit 5 that displays an analyzing result and the like. The data-processing section 3 includes, as functional blocks, a measurement data storage unit 31, a target qualification processing section for quantitative determination 32, a quantitative computation processing section 36, and a report creation processing section 37, the target qualification processing section for quantitative determination 32 including a condition setting processing section 33, an identification range calculation section 34, and a target identification processing section 35. The data-processing section 3 is actually a personal computer and the functions of the illustrated sections are implemented by the personal computer running a dedicated program for data processing installed in the computer.

In the LC-MS/MS system in the present embodiment, the mass spectrograph 2 can operate in measurement modes including MRM measurement, product-ion scan measurement, precursor-ion scan measurement, and neutral-loss scan measurement, and the description is made here assuming that the MRM measurement is performed because the MRM measurement is generally used when quantitative analysis is conducted on a known compound.

In this case, for each target compound subjected to quantitative determination, the MRM transition of a target ion (a set of the mass-to-charge ratio of a precursor ion and the mass-to-charge ratio of a product ion) and the MRM transition of one or more qualifier ions are set as analysis conditions in the mass spectrograph 2. Data acquired from the liquid chromatograph 1 and the mass spectrograph 2 under such analysis conditions is stored in the measurement data storage section 31.

Figure 2:
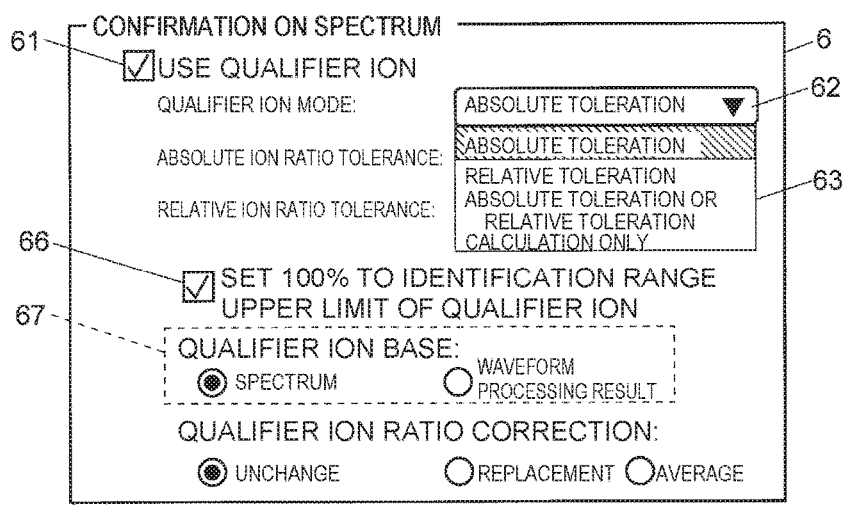
FIG. 2 is a diagram illustrating an example of a spectrum check condition setting screen in the LC-MS/MS system in the present embodiment.
Figures 3, 4, 5:
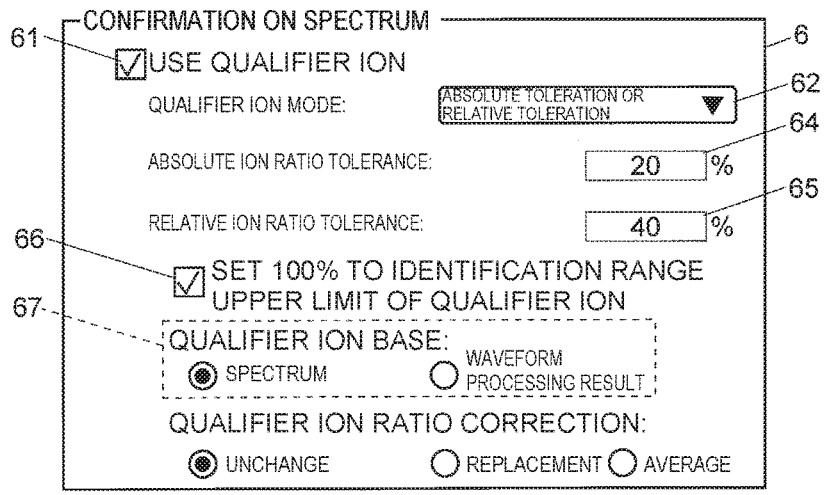
FIG. 3 is a diagram illustrating an example of a spectrum check condition setting screen in the LC-MS/MS system in the present embodiment.
FIG. 4 is a diagram illustrating an example of a qualifier ion advanced setting screen for each target ion in the LC-MS/MS system in the present embodiment.
FIG. 5 is a diagram illustrating another example of a qualifier ion advanced setting screen for each target ion in the LC-MS/MS system in the present embodiment.

With reference to FIG. 2 to FIG. 6, description is made about data processing to make a quantitative determination on a target compound based on the data collected in the previously described manner the data processing being performed using MRM measurement data obtained about a target ion and a qualifier ion for the compound. FIG. 2 and FIG. 3 are diagrams illustrating examples of a spectrum check condition setting screen of the LC-MS/MS system in the present embodiment, and FIG. 4 to FIG. 6 are diagrams illustrating examples of a qualifier ion advanced setting screen for different target ions.

In the case where, prior to quantitative analysis, it is intended to confirm using a qualifier ion whether or not a target ion truly originates from the target compound, that is, where it is intended to identify the target ion, the operator performs a predetermined operation on the input unit 4, and the condition setting processing section 33 in the target qualification processing section for quantitative determination 32 displays a spectrum check condition setting screen 6 as illustrated in FIG. 2 on a screen of the display unit 5. When intending the identification of a target ion using a qualifier ion, the operator checks a checkbox 61, "USE A QUALIFIER ION", with a clicking operation or the like of the mouse. In this case, the operator selects a qualifier ion mode.

To select the qualifier ion mode, an clicking operation on a qualifier ion mode selection button 62 causes qualifier ion modes to be displayed in the form of a drop-down menu 63 as illustrated in FIG. 2, on one of which a clicking operation may be performed as desired. Here, in the LC-MS/MS system in the present embodiment, an "ABSOLUTE TOLERATION OR RELATIVE TOLERATION" mode is provided as one of the qualifier ion modes. For example, when it is intended to conduct an analysis consistent with AORC guidelines disclosed in Non Patent Literature 2, this "ABSOLUTE TOLERATION OR RELATIVE TOLERATION" mode may be selected. In addition to this mode, an "ABSOLUTE TOLERATION" mode or a "RELATIVE TOLERATION" mode may be selected as with conventional systems.

In this example, a qualifier ion ratio reference value: 90%, an absolute tolerance: 20%, and a relative tolerance: 40% are preset as default values of parameters used when an analysis is conducted in the "ABSOLUTE TOLERATION OR RELATIVE TOLERATION" mode. Therefore, when the "ABSOLUTE TOLERATION OR RELATIVE TOLERATION" mode is selected and input, numerical values "20", and "40" are displayed in an absolute tolerance display box 64 and a relative tolerance display box 65, respectively. To change the absolute tolerance and the relative tolerance for a plurality of qualifier ions, the numerical values displayed in the absolute tolerance display box 64 and the relative tolerance display box 65 may be directly rewritten with the input unit 4. In this example, the upper limit of an identification range in the "ABSOLUTE TOLERATION OR RELATIVE TOLERATION" mode is limited to 100% by default, and thus a check mark is automatically put in a checkbox 66 "SET 100% TO THE UPPER LIMIT OF AN IDENTIFICATION RANGE FOR THE QUALIFIER ION". To eliminate this constraint, that is, to enable an identification range in excess of 100% to be set, the checkbox 66 "SET 100% TO THE UPPER LIMIT OF AN IDENTIFICATION RANGE FOR THE QUALIFIER ION" may be clicked, whereby the check mark is deleted.

In addition, the LC-MS/MS system according to the present embodiment allows the selection of whether to use, for calculating a qualifier ion ratio, the signal intensity of a peak on a mass spectrum (an ion intensity at a given time point obtained in the MRM measurement) or a signal intensity based on the peak area and the peak height of a peak (chromatogram peak) appearing on an extracted-ion chromatogram (mass chromatogram). In a qualifier ion base selection section 67 in the spectrum check condition setting screen 6, the former is used when "SPECTRUM" is selected, and the latter is used when "WAVEFORM PROCESSING RESULT" is selected, for target ion identification with the qualifier ion ratio. In the example illustrated in FIG. 2 and FIG. 3, "SPECTRUM" is selected, and thus the qualifier ion ratio is calculated based on, for example, an ion intensity obtained at a predetermined time point in the MRM measurement.

After making such settings as illustrated in FIG. 3 on the spectrum check condition setting screen 6, the operator selects and specifies a compound to be confirmed on a compound table (not illustrated), which causes the identification range calculation section 34 to calculate the identification ranges of each of qualifier ions for a target ion (an MRM transition for the target ion) set for the specified compound.

Specifically, the identification range calculation section 34 calculates an identification range Pa in the absolute toleration mode using Equation (1), and calculates an identification range Pr in the relative toleration mode using Equation (2). The calculations result is as follows.

$$Pa=Ri \pm Rw[\%]=90 \pm 20[\%]$$

$$Pr=Ri \pm (Ri \times Rw)/100[\%]==90 \pm (90 \times 0.4)=90 \pm 36[\%]$$

Thus, these two identification ranges are compared, and a greater one is selected. Since Pr>Pa is satisfied in the above example, Pr is selected as the identification range. Note that this selected identification range is 54 to 126[%], the upper limit value of which exceeds 100[%], and thus the upper limit is set at 100[%], and a final identification range is determined to be 54 to 100[%].

The identification range calculation section 34 displays MRM transitions, parameters, and calculated identification ranges for qualifier ions set for the specified compound, in the form of a parameter table 71 in a qualifier ion advanced setting screen 7 as illustrated in FIG. 4. The example illustrated in FIG. 4 is a screen displayed when all of the qualifier ion ratio reference values, the absolute tolerances, and the relative tolerances are their respective default values previously described for three qualifier ions associated with a target ion the MRM transition for which is 414.20>183.10 (precursor ion m/z: 414.20, the product ion m/z: 183.10). The term "DEFAULT" illustrated in an absolute tolerance display column 74 and a relative tolerance display column 75 means that numerical values displayed in the absolute tolerance display box 64 and the relative tolerance display box 65 in the spectrum check condition setting screen 6 is to be used. In the example illustrated in FIG. 4, the three qualifier ions share a common qualifier ion ratio reference value, absolute tolerance, and relative tolerance, and thus have an identical identification range.

Into a qualifier ion reference value display column 73, the absolute tolerance display column 74, and the relative tolerance display column 75 in the parameter table 71 in the qualifier ion advanced setting screen 7, any numerical value can be input by an input operation using the input unit 4, for each qualifier ion. FIG. 5 illustrates an example in which, for five qualifier ions, qualifier ion ratio reference values are made different from one another, and the absolute tolerance and the relative tolerance are both changed to "60". When any one of these three parameters is changed, the identification range is also changed, and thus the identification range calculation section 34 recalculates the identification ranges based on the changed parameters and updates the numerical values in the identification range display column 76.

For example, for a qualifier ion the MRM transition for which is 130.00>29.00, $$Pa=Ri \pm Rw[\%]=200 \pm 60[\%]$$

$$Pr=Ri \pm (Ri \times Rw)/100[\%]=200 \pm (200 \times 0.6)=200 \pm 120 [\%]$$

are calculated, and thus Pr is selected as the identification range. Since this selected identification range is 80 to 320[%], the upper limit value thereof is limited to 100[%], and the final identification range is set at 80 to 100[%]. In addition, for a qualifier ion the MRM transition for which is 130.00>27.00, $$Pa = Ri \pm Rw[\%] = 300 \pm 60[\%]$$

$$Pr = Ri \pm (Ri \times Rw)/100[\%] = 300 \pm (300 \times 0.6) = 300 \pm 180 [\%]$$

are calculated, and thus Pr is selected as the identification range. In this case, since this selected identification range is 120 to 480[%], the lower limit value of the identification range exceeds 100%. Therefore, the entire identification range exceeds 100%, which means that the identification of a target ion using the identification range is impossible. Thus, to indicate this fact, the text "ABOVE UPPER LIMIT" is displayed in the identification range display column 76.

As seen from the above, in the identification range display column 76 in the parameter table 71 in the qualifier ion advanced setting screen 7, the identification ranges of a plurality of qualifier ions for a given target ion are displayed in the form of numerical values, and if the identification range is inappropriate for identification, "ABOVE UPPER LIMIT" is displayed. This allows the operate to confirm the identification range of each qualifier ion at once, as well as to recognize that an identification range is inappropriate and to adjust a parameter such as the qualifier ion ratio reference value as appropriate.

Meanwhile, in the case where the "ABSOLUTE TOLERATION" mode or the "RELATIVE TOLERATION" mode are selected and input as the qualifier ion mode in place of the "ABSOLUTE TOLERATION OR RELATIVE TOLERATION" mode, there is only one tolerance to set for the operator. Thus, in this case, the identification range calculation section 34 displays, as illustrated in FIG. 6, the qualifier ion advanced setting screen 7 including the parameter table 71 provided with a single tolerance display column 77 on the screen of the display unit 5. That is, in this case, the qualifier ion advanced setting screen 7 becomes the same as the table on the conventional qualifier ion advanced setting screen illustrated in FIG. 9. Therefore, displaying and operability in using the "ABSOLUTE TOLERATION" mode or the "RELATIVE TOLERATION" mode provided also in conventional systems are the same as in conventional practices, which can prevent an operator accustomed to operate the conventional systems from being confused or making a mistake.

As previously described, upon the identification range is determined for each of qualifier ions, the target identification processing section 35 reads measurement data on a target compound stored in the measurement data storage section 31 and calculates a qualifier ion ratio in an actual measurement from the signal intensity of a spectral peak for a target ion and the signal intensities of spectral peaks for the qualifier ions. Then, it is determined whether or not the calculated qualifier ion ratios in the actual measurement fall within their respective identification ranges set for the qualifier ions, and when the calculated qualifier ion ratios fall within their respective identification ranges, an obtained estimation result is that there is a high possibility of the target ion originating from the target compound. The target identification processing section 35 determines whether or not an actually measured qualifier ion ratio falls within an identification range for each of qualifier ions associated with one target ion to obtain the result of whether or not the target ion is identified.

When "WAVEFORM PROCESSING RESULT" is selected in the qualifier ion base selection section 67 in the spectrum check condition setting screen 6, the target identification processing section 35 creates, for a target ion and for each qualifier ion, an extracted-ion chromatogram from MRM measurement data and performs peak detection on the chromatogram to determine chromatogram peaks. Then, the area value and the height value (or one of them) of each of the peaks are calculated, and calculates qualifier ion ratios using ratios between area values and height value of peaks as the values of signal intensities, for example. The calculation of the qualifier ion ratio is not limited to this.

When the target ion is clearly determined to originate from a target compound by the target identification processing section 35, the quantitative computation processing section 36 creates the extracted-ion chromatogram of the target ion based on the measurement data, and determines a quantitative value (concentration value) using a calibration curve created in advance from the area value of a chromatogram peak corresponding to the target compound. This allows the avoidance of performing an inappropriate quantitative computation using an erroneous target ion not originating from the target compound. In addition, using the "ABSOLUTE TOLERATION OR RELATIVE TOLERATION" mode allows the confirmation of a target ion consistent with AORC guidelines, which is very cumbersome, to be simply performed.

By the operator performing a predetermined operation on the input unit 4, the report creation processing section 37 creates a report containing specified contents including a graph illustrating measurement results such as a chromatogram, and a quantitative analysis result. At this point, the contents of the report can contain an identification range for each of qualifier ions used for the confirmation of a target ion. The report created in such a manner can be confirmed on the screen of the display unit 5 and additionally printed out from a printer (not illustrated).

The data-processing system using for the LC-MS/MS system of the above embodiment is configured to calculate identification ranges based on tolerances and qualifier ion ratio reference values set by default or input (changed) by an operator, and may be configured to determine the identification ranges from given qualifier ion ratio reference values based on a correspondence table between qualifier ion ratio reference value and identification range created in advance. FIG. 7 illustrates an example of a correspondence table between qualifier ion ratio reference value and identification range.

Now, assuming that the qualifier ion ratio reference value of a qualifier ion for a certain target ion is set at 45[%], the identification range calculation section 34 refers to the correspondence table illustrated in FIG. 7 and derives therefrom an identification range of 5 to 60[%]. Alternatively, assuming that the qualifier ion ratio reference value is set at 80[%], the identification range calculation section 34 refers to the correspondence table illustrated in FIG. 7 and derives therefrom an identification range of 30 to 95[%]. Then, the derived identification range is determined, as it is, to be a final identification range. This allows an operator to determine an identification range corresponding to qualifier ion ratio reference value without inputting parameters such as a tolerance one by one and without selecting a qualifier ion mode.

It should be noted that the previously described embodiment is a mere example of the present invention, and any change, modification or addition appropriately made within the spirit consistent with the present invention will evidently fall within the scope of claims of the present patent application.

For example, in the previously described embodiment, the data-processing system according to the present invention is applied to the LC-MS/MS system, but the mass spectrograph need not be capable of MS/MS measurement. In addition, the data-processing system according to the present invention is evidently applicable to a GC-MS or a GC-MS/MS, a combination of a gas chromatograph and a mass spectrograph.

REFERENCE SIGNS LIST

1 . . . liquid chromatograph
2 . . . mass spectrograph
3 . . . data-processing section
31 . . . measurement data storage section
32 . . . target qualification processing section for quantitative determination
33 . . . condition setting processing section
34 . . . identification range calculation section
35 . . . target identification processing section
25 36 . . . quantitative computation processing section
37 . . . report creation processing section
4 . . . input unit
5 . . . display unit
6 . . . spectrum check condition setting screen
61 . . . checkbox "USE A QUALIFIER ION"
62 . . . qualifier ion mode selection button
63 . . . drop-down menu
64 . . . absolute tolerance display box
65 . . . relative tolerance display box
66 . . . checkbox "SET 100% TO THE UPPER LIMIT OF AN IDENTIFICATION RANGE FOR THE QUALIFIER ION"
7 . . . qualifier ion advanced setting screen
71 . . . parameter table
72 . . . MRM transition display column
73 . . . qualifier ion reference value display column
74 . . . absolute tolerance display column
75 . . . relative tolerance display column
76 . . . identification range display column

The invention claimed is:

1. A data-processing system for mass-spectrometry, comprising:
a processor configured to
calculate a signal intensity of a target ion included in a target compound through measurement of a target sample;
calculate a signal intensity of a predetermined qualifier ion also included in the target compound through measurement of the target sample, the qualifier ion having a different mass-to-charge ratio from that of the target ion;
allow a user to select between a first mode, a second mode, and a third mode, the first mode being a mode in which a tolerance of a qualifier ion ratio is determined in a form of an absolute value of the ratio, the second mode being a mode in which a tolerance of a qualifier ion ratio is determined in a form of a relative value of the ratio, and the third mode being a mode in which a tolerance of a qualifier ion ratio is selected from one of an identification range of a qualifier ion ratio determined in a form of an absolute value of the ratio and an identification range of a qualifier ion ratio determined in a form of a relative value of the ratio according to comparison between the identification ranges; the qualifier ion ratio being an intensity ratio between a signal intensity of the target ion and a signal intensity of the qualifier ion; and
when the third mode is selected, calculate a first identification range of the qualifier ion ratio based on an absolute tolerance given as an absolute value of the ratio, calculate a second identification range of the qualifier ion ratio based on a relative tolerance given as a relative value of the ratio with respect to a standard qualifier ion ratio for a qualifier ion of interest, select one of the two identification ranges, the first and second identification ranges, according to a comparison between the first and second identification ranges, determine the selected identification range to be an identification range used to determine an actually measured qualifier ion ratio, and determine whether or not a peak on a mass spectrum supposed to be a peak of the target ion truly originates from the target compound based on the selected identification range, whereby an appropriateness of the target ion is confirmed.

2. The data-processing system for mass-spectrometry according to claim 1, wherein the processor is further configured to allow a user to input the absolute tolerance and the relative tolerance for each qualifier ion in a case of determining a plurality of qualifier ions for one target ion.

3. The data-processing system for mass-spectrometry according to claim 2, wherein the processor is further configured to allow a user to specify an upper limit and/or a lower limit of the identification range to determine the actually measured qualifier ion ratio.

4. The data-processing system for mass-spectrometry according to claim 3, wherein the processor is further configured to narrow the identification range in accordance with a predetermined upper limit value or lower limit value when the upper limit and/or the lower limit is specified by the range limit setting section.

5. The data-processing system for mass-spectrometry according to claim 4, wherein the processor is further configured to allow a user to be notified of a fact that the upper limit and/or a lower limit is specified by the range limit setting section, and the calculated entire identification range falls out of a range constrained by a predetermined upper limit value or lower limit value.

6. The data-processing system for mass-spectrometry according to claim 3, wherein the processor is further configured to allow a user to be notified of a fact that the upper limit and/or a lower limit is specified by the range limit setting section, and the calculated entire identification range falls out of a range constrained by a predetermined upper limit value or lower limit value.

7. The data-processing system for mass-spectrometry according to claim 2, wherein the processor is further configured to output the identification range determined by the identification range determination section in a form of a report.

8. The data-processing system for mass-spectrometry according to claim 1, wherein the processor is further configured to allow allows a user to specify an upper limit and/or a lower limit of the identification range to determine the actually measured qualifier ion ratio.

9. The data-processing system for mass-spectrometry according to claim 8, wherein the processor is further configured to narrow the identification range in accordance with a predetermined upper limit value or lower limit value when the upper limit and/or the lower limit is specified by the range limit setting section.

10. The data-processing system for mass-spectrometry according to claim 9, wherein the processor is further configured to allow a user to be notified of a fact that the upper limit and/or a lower limit is specified by the range limit setting section, and the calculated entire identification range falls out of a range constrained by a predetermined upper limit value or lower limit value.

11. The data-processing system for mass-spectrometry according to claim 9, wherein the processor is further configured to output the identification range determined by the identification range determination section in a form of a report.

12. The data-processing system for mass-spectrometry according to claim 8, wherein the processor is further configured to allow allows a user to be notified of a fact that the upper limit and/or a lower limit is specified by the range limit setting section, and the calculated entire identification range falls out of a range constrained by a predetermined upper limit value or lower limit value.

13. The data-processing system for mass-spectrometry according to claim 12, wherein the processor is further configured to output the identification range determined by the identification range determination section in a form of a report.

14. The data-processing system for mass-spectrometry according to claim 8, wherein the processor is further configured to output the identification range determined by the identification range determination section in a form of a report.

15. The data-processing system for mass-spectrometry according to claim 1, wherein the processor is further configured to output the identification range determined by the identification range determination section in a form of a report.

16. A non-transitory computer readable media recording a program, running on a computer for mass-spectrometry, the program causing the computer to:
calculate a signal intensity of a target ion included in a target compound through measurement of a target sample;
calculate a signal intensity of a predetermined qualifier ion also included in the target compound through measurement of the target sample, the qualifier ion having a different mass-to-charge ratio from that of the target ion;
allow a user to select between a first mode, a second mode, and a third mode, the first mode being a mode in which a tolerance of a qualifier ion ratio is determined in a form of an absolute value of the ratio, the second mode being a mode in which a tolerance of a qualifier ion ratio is determined in a form of a relative value of the ratio, and the third mode being a mode in which a tolerance of a qualifier ion ratio is selected from one of an identification range of a qualifier ion ratio determined in a form of an absolute value of the ratio and an identification range of a qualifier ion ratio determined in a form of a relative value of the ratio according to comparison between the identification ranges, the qualifier ion ratio being an intensity ratio between a signal intensity of the target ion and a signal intensity of the qualifier ion; and
when the third mode is selected, calculate a first identification range of the qualifier ion ratio based on an absolute tolerance given as an absolute value of the ratio, calculate a second identification range of the qualifier ion ratio based on a relative tolerance given as a relative value of the ratio with respect to a standard qualifier ion ratio for a qualifier ion of interest, select one of the two identification ranges, the first and second identification ranges, according to a comparison between the first and second identification ranges, determine the selected identification range to be an identification range used to determine an actually measured qualifier ion ratio, and determine whether or not a peak on a mass spectrum supposed to be a peak of the target ion truly originates from the target compound based on the selected identification range, whereby an appropriateness of the target ion is confirmed.

17. A mass spectrometry method, comprising:
calculating a signal intensity of a target ion included in a target compound through measurement of a target sample;
calculating a signal intensity of a predetermined qualifier ion also included in the target compound through measurement of the target sample, the qualifier ion having a different mass-to-charge ratio from that of the target ion;
allowing a user to select between a first mode, a second mode, and a third mode, the first mode being a mode in which a tolerance of a qualifier ion ratio is determined in a form of an absolute value of the ratio, the second mode being a mode in which a tolerance of a qualifier ion ratio is determined in a form of a relative value of the ratio, and the third mode being a mode in which a tolerance of a qualifier ion ratio is selected from one of an identification range of a qualifier ion ratio determined in a form of an absolute value of the ratio and an identification range of a qualifier ion ratio determined in a form of a relative value of the ratio according to comparison between the identification ranges, the qualifier ion ratio being an intensity ratio between a signal intensity of the target ion and a signal intensity of the qualifier ion; and
when the third mode is selected, calculating a first identification range of the qualifier ion ratio based on an absolute tolerance given as an absolute value of the ratio, calculating a second identification range of the qualifier ion ratio based on a relative tolerance given as a relative value of the ratio with respect to a standard qualifier ion ratio for a qualifier ion of interest, selecting one of the two identification ranges, the first and second identification ranges, according to a comparison between the first and second identification ranges, determining the selected identification range to be an identification range used to determine an actually measured qualifier ion ratio; and determining whether or not a peak on a mass spectrum supposed to be a peak of the target ion truly originates from the target compound based on the selected identification range, whereby an appropriateness of the target ion is confirmed.

* * * * *